United States Patent [19]

Boulter et al.

[11] Patent Number: 4,640,836

[45] Date of Patent: Feb. 3, 1987

[54] PLANT PROTECTION METHOD

[75] Inventors: Donald Boulter, Durham; Angharad M. R. Gatehouse; John A. Gatehouse, both of Broom Park; Roger B. Cox, Reading, all of England

[73] Assignee: Agricultural Genetics Company, Limited, Cambridge, England

[21] Appl. No.: 639,856

[22] Filed: Aug. 13, 1984

[30] Foreign Application Priority Data

Aug. 19, 1983 [GB] United Kingdom ................. 8322446
Nov. 18, 1983 [GB] United Kingdom ................. 8330847

[51] Int. Cl.[4] ............................................. A01N 65/00
[52] U.S. Cl. ................................................. 424/195.1
[58] Field of Search ............................. 424/195, 195.1

[56] References Cited

PUBLICATIONS

Chem. Abstrs. 92:125,198t, 1980.
Chem. Abstrs. 95:57066s, 1981.

Primary Examiner—Donald B. Moyer
Assistant Examiner—John W. Rollins, Jr.
Attorney, Agent, or Firm—Oblon, Fisher, Spivak, McClelland & Maier

[57] ABSTRACT

A trypsin inhibitor derived from the cowpea *Vigna unguiculata* or similar plant is used to protect another plant or a part thereof from attack by a pest of that plant. The plant protected may in particular be cotton or a cereal crop and particular pests from which the plant is protected are bollworms of the genus *Heliothis*.

4 Claims, No Drawings

PLANT PROTECTION METHOD

This invention relates to the protection of plants against pests. It is especially concerned with the protection of cotton and cereals but is also applicable to other plants for which field pests and storage pests constitute a serious economic problem.

Cotton is characterised by a high susceptibility to certain pests such as insects, and its production entails very heavy costs for protective treatment by means of the insecticides which are currently available. One major group of cotton pests is that of the bollworms of the genus Heliothis of which *Heliothis virescens* is a most destructive representative species found throughout the cotton growing region of the USA and South America as well as in parts of Africa. Indeed the Heliothis bollworms are pests of a wide variety of plant families in addition to cotton and including many cereals such as maize and sorghum as well as other types of plant including tobacco, phaseolus, soya bean and sunflower. For example *Heliothis armigera* and *Heliothis zea* attack both cotton and cereals. Other serious pests of the cotton plant are the bollweavils Anthonomus of which the species *Anthonomus grandis* can be found in the cotton growing regions of the southern states of the USA, Mexico and parts of the Caribbean. The larvae of both Heliothis and Anthonomus genera are responsible for severely affecting cotton yields since they feed within the cotton squares (buds) and bolls resulting in death and shedding of the squares and small bolls: in the larger bolls the lint becomes stained and decayed. The adults of Anthonomus spp also feed on the cotton flowers, squares and bolls. Another group of cotton pests are the cotton stainers Dysdercus spp which when carrying spores of the fungus *Nematospora gossypii* can completely spoil the cotton crop.

Cotton and cereals are also affected by other insect genera which are distinct from Heliothis and Anthonomus. These include, for example, those of the genus Tribolium, e.g. *Tribolium confusum* a storage pest of the grain of wheat and maize and also the genus Sitophilus, e.g. *Sitophilus granarius, Sitophilus oryzae* and *Sitophilus zeamais* which are serious storage pests not only of wheat and maize, but also of rice and sorghum. This genus is virtually cosmopolitan. Other major cereal pests are those of the genus Chilo including for example *Chilo partellus* which is dominant in Africa and India and for which host plants are maize, sorghum, millet, sugarcane and rice. Another species of this group, *Chilo suppressalis,* is a serious pest of rice and maize in China and Japan. Yet another insect genus presenting a serious problem in the growing of maize, rice, sorghum, cotton and tobacco is the genus Spodoptera including for example *Spodoptera exempta, Spodoptera frugiperda, Spodoptera littoralis* and *Spodoptera litura.* Other important pests are found in the genus Ostrinia, e.g. *Ostrinia nubilalis* and *Ostrinia furnacalis* which affect maize and sorghum and have a wide geographical distribution, being found in Europe, the mediterranean region (including the Near East), Eastern USA, South East Asia, Central and East Asia and Australasia.

In spite of the availability of a wide range of pesticides these pests remain a serious problem. Many pesticides have the severe disadvantages of high toxicity towards humans and animals, relatively high phytotoxicity to plants, and increasing insect resistance.

It has now been found that naturally occurring trypsin inhibitors present in one plant species and effective against the insect predators of that plant can exhibit a powerful and surprising toxicity towards pests in plants in which they are not produced. In particular it has been found that trypsin inhibitors produced by a species of legume are toxic towards pests of the plant genera mentioned above.

The present invention comprises a method of protecting plants or parts thereof against invading pests in which the pest invading the plant or parts thereof is presented with a pesticidally effective amount of one or more of the trypsin inhibitors derived from the cowpea or similar plant.

The method of the present invention is particularly useful in protecting non-leguminous plants against invading pests by the use of a trypsin inhibitor derived from a leguminous plant.

Particularly preferred trypsin inhibitors are those of *Vigna unguiculata,* one common name of which is the cowpea. It is also known as the black-eyed pea.

The method is applicable to the protection of plants or any part thereof, including seeds derived from the plants, which are susceptible to being attacked by pests.

In particular this method is applicable to the protection of cotton and cereals and also to any plant susceptible to pests of the genera Heliothis, Anthonomus, Tribolium, Sitophilus, Chilo, Spodoptera, Ostrinia and Agrotis.

The presentation of a pesticidally effective amount of one or more trypsin inhibitors may be achieved by external application of said inhibitor to said plants or parts thereof either directly or in the vicinity of said plants or parts to be protected.

The inhibitor may be applied in a wide variety of forms which includes powders, crystals, suspensions, emulsified suspensions, dusts, pellets, granules, aerosols, baits, solutions and/or other liquids, gels, or other dispersions.

The present invention therefore also provides a composition for application to plants or parts thereof comprising one or more plant-derived trypsin inhibitors in particular cowpea trypsin inhibitors and an agricultural adjuvant.

The compositions according to the present invention are generally applied to the plant or part thereof, in particular a seed, including seeds in storage in an agricultural formulation which also comprises an agriculturally acceptable carrier. By the term "agriculturally acceptable carrier" is meant a substance which may be used to dissolve, disperse or diffuse an active compound in the composition without impairing the effectiveness of the compound and which by itself has no detrimental effect on the soil, equipment, crops or agronomic environment. The compositions according to the present invention may be either solid or liquid formulations or solutions. For example, the compounds may be formulated as wettable powders, or a concentrate which is emulsifiable.

It is often desirable to include adjuvants, such as wetting agents, spreading agents, dispersing agents, stickers and adhesives, in accordance with conventional agricultural practices.

For the preparation of emulsifiable concentrates, one or more of the active ingredients may be dissolved in one or more organic solvents, such as benzene, toluene, xylene, methylated naphthalene, corn oil, pine oil, o-dichlorobenzene, isophorone, cyclohexane and methyl oleate, or mixtures thereof, together with an emulsifying agent which permits dispersion in water.

Wettable powders suitable for spraying may be prepared by admixing one or more of the active ingredients with a finely divided solid, such as clays, inorganic silicates and carbonates and silicas, and by incorporating wetting agents, sticking agents and/or dispersing agents in such mixtures.

Dusts may be prepared by mixing the active ingredients according to the present invention with one or more finely divided inert solids which may be organic or inorganic in nature. Materials useful for this purpose include, for example, botanical flours, silicas, silicates, carbonates and clays. One convenient method of preparing a dust is to dilute a wettable power with a finely divided carrier.

The preferred trypsin inhibitors are those present in the cowpea *Vigna unguiculata* and can be extracted from the seed by a variety of methods. Some of these inhibitors also possess chymotrypsin inhibitory activity. The nature and properties of the inhibitors and their isolation from the cowpea have been described in the following publications:

(1) Biochemical basis of insect resistance in *Vigna unguiculata*, J. Sci. Food Agric. 1979, 30, 948–958;
(2) Isolation and characterisation of trypsin inhibitors from cowpea, (*Vigna unguiculata*), Phytochem 1980, 19, 751–756.

The inhibitors fall into two distinct groups each of which comprises a number of closely related "isoinhibitors" which may be of independent origin or may include artifacts. The first of such groups inhibits trypsin only while the second show activity against chymotrypsin as well as against trypsin. Some of the characteristics of these protein inhibitors are tabulated below.

| CHARACTERIZATION OF COWPEA TRYPSIN INHIBITORS (CPTI) | | | | | |
|---|---|---|---|---|---|
| Material | Mr | pI | Sub-unit structure | Binding sites/ molecule | Molecular combining weight with trypsin[a] | Molecular combining weight with chymotrypsin[b] |
| Total CPTI (~80% CPTI (A)) (~20% CPTI (B)) | 17,000 | 4–5 (7 bands) | Dimer | — | 9,200 | 96,000 |
| CPTI (A) (Trypsin only) | 12–15,000 | 4.5–5.0 (4 bands) | Dimer | 2 trypsin | 8,100 | — |
| CPTI (B) (Trypsin + chymotrypsin) | 16–20,000 | 4.0–4.2 (3 bands) | Dimer | 1 trypsin 1 chymotrypsin | 12,500 | 19,000 (calculated from above) |

[a]from reaction with active site titration reagent
[b]calculation from inhibition curve Amino acid composition of total cowpea trypsin inhibitor, the trypsin-only inhibitor and the double-headed trypsin-chymotrypsin inhibitor, are given below:

| Amino acid | Total cowpea trypsin inhibitor Mol % | Trypsin-chymotrypsin inhibitor Mol % | Trypsin only inhibitor Mol % |
|---|---|---|---|
| Aspartic acid | 14.7 | 15.9 | 13.9 |
| Threonine | 4.6 | 4.5 | 5.0 |
| Serine | 10.2 | 10.2 | 11.9 |
| Glutamic acid | 9.9 | 10.2 | 9.6 |
| Glycine | 1.9 | 3.0 | 1.3 |
| Alanine | 3.5 | 6.0 | 2.7 |
| Valine | 0.9 | 1.2 | 0.6 |
| Methionine | 1.5 | 0 | 1.9 |
| Isoleucine | 5.4 | 4.4 | 5.8 |
| Leucine | 2.8 | 1.5 | 2.7 |
| Tyrosine | 1.0 | 1.7 | 1.0 |
| Phenylalanine | 2.1 | 4.3 | 1.4 |
| Lysine | 6.5 | 5.8 | 6.6 |
| Histidine | 5.3 | 5.0 | 5.7 |
| Arginine | 5.1 | 4.0 | 5.3 |
| Cystine | 17.4 | 15.8 | 17.8 |
| Proline | 7.0 | 7.0 | 7.0 |
| Tryptophan | 0 | 0 | 0 |

Means of two or more determinations.

High levels of these inhibitors are responsible for the resistance of certain varieties of the cowpea to the bruchid beetle *Callosobruchus maculatus*. The inhibitor content of cowpea varieties ranges from 0.2 to 0.4% by weight in susceptible varieties to 0.9% in the resistant variety as described in the first publication mentioned above. In practice, because of its ease of availability, a more convenient source of inhibitor is the black-eyed pea obtainable commercially in the USA even though it has a rather low content (0.4%) of inhibitors. The mode of action of the inhibitors against the larvae of the bruchid beetle is considered to be anti-nutritional. Trypsin-like enzymes are primary digestive enzymes which enable the insects to feed and therefore their inhibition causes starvation. The corresponding mode of action against cotton pests may be similar. It is important to note, however, that other trypsin inhibitors, e.g. those from soya bean and lima bean, have no corresponding effect on these pests. The range of specificity of the cowpea inhibitory material as anti-nutritional proteins is therefore crucial to its unexpected effectiveness against cotton and cereal pests.

Assessment of the biological properties of the inhibitors has been mainly carried out using the total trypsin inhibitor fraction of the cowpea after purification by means of affinity chromatography on trypsin-linked gel columns. Use of the total fraction is likely to be the preferred method of controlling pests.

The publications referred to above may be consulted for details of the extraction of the trypsin inhibitors but for convenience a short summary of the method is now given.

PURIFICATION OF COWPEA TRYPSIN INHIBITOR FRACTIONS BY AFFINITY CHROMATOGRAPHY (1) Preparation of resin for trypsin affinity chromatography A column of trypsin linked to cyanogen bromide-activated Sepharose 4B was prepared according to the Method of March et al. Anal. Biochem. (1974) 60: 149.

Packed Sepharose 4B beads (600 ml) were suspended in an equal volume of distilled water to which aqeuous sodium carbonate (2M, 1200 ml) was added. The slurry was gently stirred. On addition of a solution of CNBr in acetonitrile (2 g/ml, 78 ml) the slurry was stirred vigorously for 2 minutes. The CNBr-activated Sepharose was then poured on to a course sintered glass filter and the filtrate inactivated by allowing it to pour into sodium hypochlorite solution (2% v/v). The activated resin was then taken through the following series of washes:

(1) 0.1M $NaHCO_3$:0.1M $Na_2CO_3$=1:1
(2) Distilled $H_2O$
(3) 0.1M $NaHCO_3$ the resin being dried to a moist cake between washes. After the final wash the resin was transferred to 0.1M $NaHCO_3$ (1200 ml) containing bovine trypsin (6 g, sigma). The slurry was then rotated for 24 hours at 4° C. to facilitate coupling of the enzyme. Following the coupling reaction the resin was again filtered and the optical density and volume of the filtrate measured. It was then possible to calculate the amount of bound trypsin. The resin was finally taken through the series of buffers used in the purification of the trypsin inhibitor.

(2) Preparation of seed meals

Mature, dry seeds of cowpea (*Vigna unguiculata*) were ground for 2 minutes in a Janke and Kunkel water-cooled mill; both the testa and cotyledons were used. The resulting meal would pass through a 423 μm mesh.

(3) Purification of total cowpea trypsin inhibitor

The meal (400 g) was extracted overnight at room temperature in 0.1M sodium acetate buffer (1200 ml) pH 4.0 containing 0.3M NaCl, 0.01M $CaCl_2$. The extract was then centrifuged at 15,000 g for 20 minutes at 15° C. and the supernatant filtered through Whatman No. 1 filter paper. The filtrate was then loaded on to the column of trypsin linked to CNBr-activated Sepharose 4B (660 ml volume) previously packed and equilibrated with acetate buffer, pH 4.0 as described above. After application of the filtrate, the column was washed with the same buffer to remove all non-bound protein followed by an unbuffered wash (0.3M NaCl, 0.01M $CaCl_2$). The trypsin inhibitor was eluted from the column with HCl (0.01M), pH 2.1, containing 0.3M NaCl, 0.01M $CaCl_2$, at a flow rate of 70 ml/hr.

The fractions containing purified inhibitor were pooled and precipitated with ammonium sulphate to 90% saturation at 40° C. The precipitated protein was centrifuged at 15,000 g for 20 minutes at 4° C. The pellet was then resuspended in a minimum volume of 0.1M $NH_4HCO_3$ and desalted on a gel filtration column of Sephadex G-25 fine, 3.2 cm diameter×60 cm length (480 ml volume), which was packed and equilibrated with 0.1M $NH_4HCO_3$. Flow of buffer through the column was controlled to give a flow rate of 45 ml/hr. The trypsin inhibitor peak was then pooled, frozen in liquid air and lyophilised (freeze-drying removes the buffer components in the form of gaseous $CO_2$ and $NH_3$).

The specific activity of the purified inhibitor was determined using the synthetic trypsin substrate α-N-benzoyl-DL-arginine p-nitroanilide (BAPNA) by the method of Erlanger et al., (1961). Archives Biochem. Biophys. 95: 271.

(4) Separation of trypsin and chymotrypsin-trypsin inhibitors

The trypsin and chymotrypsin-trypsin inhibitors were separated by affinity chromatography on a column of chymotrypsin linked to Sepharose using the same buffer systems and experimental conditions as previously described for the isolation of the total trypsin inhibitor fraction. The unbound fraction was active against trypsin but devoid of chymotrypsin inhibitory activity, whereas the fraction which bound and was subsequently eluted at pH 2.1 contained inhibitory activity towards both trypsin and chymotrypsin. As with the total inhibitor fraction the trypsin and chymotrypsin-trypsin inhibitors were desalted by gel filtration on Sephadex G-25 fine. The ratio of the two inhibitor fractions was approximately 1:4 chymotrypsin-trypsin:trypsin.

In utilising cowpea inhibitor protein for the protection of plants according to the present invention the active material is presented so that it is consumed by the invading pest and therefore the presence of the inhibitor in the closest possible association with the plant, on or in the plant leaves and other tissues, is necessary. Particularly vulnerable to attack by the two major pests, Heliothis and Anthonomus, are the developing cotton squares, bolls and terminal buds and therefore it is essential that the inhibitor is deployed in a manner which affords protection to these tissues. It is desirable to achieve a concentration of inhibitor of at least 1% by weight of plant tissue. One method of application is to treat plants with the trypsin inhibitor in a suitable formulation as indicated above but other methods of presenting the active material to the invading pest may also be developed. An example of the treatment of plants by spraying a liquid preparation containing inhibitor material will now be given.

METHOD OF INSECTICIDAL APPLICATION

The insecticidal action of the total trypsin inhibitor fraction (CPTI), as purified by affinity chromatography, was demonstrated on a commercial Stoneville variety of cotton against the cotton pest, *Heliothis virescens* (bollworm).

Cultures of *H. virescens* were reared on a bean/alfalfa based artificial diet and maintained in a controlled environment at 25° C. with a 14 hour light, 10 hour dark regime. The cotton was reared from seed in a controlled environment growth cabinet (28° C., 14 hour light). The inhibitor fraction (100.5 mg) was dissolved in distilled water (4 ml) and sprayed on to the developing cotton squares (which remained intact on the plant), the tissue being dried by a flow of warm air between applications. A maximum of 10 mg of CPTI was applied per square.

The following experiments were set up on a single cotton plant:

| | |
|---|---|
| Treatment (A) | Experimental I: Square + CPTI + larvae |
| Treatment (B) | Experimental II: Free choice experiment |

-continued

| | | |
|---|---|---|
| (a) | Square + CPTI + larvae | |
| (b) | Square + H₂O + larvae | |
| Treatment (C) | Control I: | |
| | Square + H₂O + larvae | |
| Treatment (D) | Control II: determination of the inherent effect of CPTI on the square | |
| | Square + CPTI: no larvae | |

Five 3 to 4-day old larvae were transferred from an artificial diet to each of the treated cotton squares. These were then bagged using nylon mesh (aperture, 20 microns) so as to ensure no insect escape. In the case of the free choice experiment the two squares (one with CPTI, the other with H₂O) were bagged together.

The plant was then placed in a ventilated insect proof cage, which in turn was placed in a controlled environment chamber. After five days the experiment was terminated and the squares examined.

RESULTS

| TREATMENT | | CONDITION OF SQUARE | LARVAE |
|---|---|---|---|
| (A) | + CPTI + larvae | No square abscission; Bracts + flower bud undamaged. | No surviving larvae |
| (B) | | | |
| (a) | + CPTI + larvae | No square abscission. Bud in perfect condition; two minute holes in bracts | Dead larvae on bracts |
| (b) | + H₂O + larvae | Square abscissed; holes in bracts and lower part of bud eaten. | Larvae feeding in bud |
| (C) | + H₂O + larvae | No square abscission, but bracts and flower bud damaged by larval holes and larvae were present in the bud. Both bud and bracts had gone brown and limp. | Larvae feeding in bud |
| (D) | + CPTI No larvae | Square in perfect condition. | |

The following example shows the toxicity of the cowpea inhibitor to a serious cereal pest.

EFFECT OF CPTI ON DEVELOPMENT OF TRIBOLIUM CONFUSUM

Total cowpea trypsin inhibitor fraction, as purified by trypsin affinity chromatography, was incorporated into wheat meal at 0% (control), 2.5%, 5.0% and 7.5% by weight. The inhibitor was dissolved in an excess volume of distilled water and added to the meal so as to form a suspension thus ensuring thorough mixing of the antimetabolite. Water was added to the control diet in a similar fashion. All diets were then freeze-dried. The freeze-dried diets were re-equilibrated for 7 days at 30° C., 70% rh. (5×1 g replicas were carried out per treatment).

After the diets had re-equilibrated each replica was inoculated with 5 sexually mature adult insects for 5 days. All individuals were allowed to develop to the adult stage and therefore 90 days was allowed for the developmental period.

RESULTS

| Treatment | Number of Adults | % Adults Relative to control |
|---|---|---|
| CONTROL I (0% CPTI) | 39 | 100 |
| CONTROL II (0% CPTI) | 40 | 100 |
| +2.5% CPTI | 2 | 5 |
| +5.0% CPTI | 3 | 7.6 |
| +7.5% CPTI | 2 | 5 |

These results demonstrate that the CPTI inhibitor is very toxic to *Tribolium confusum* reducing adult survival to only 5% relative to the controls. Similar experiments carried out whereby the developmental period given was of a shorter time (i.e. so as not to allow all individuals to develop to maturity) showed that the inhibitor also increased the developmental period of a given organism. This increase in developmental time is also another important criterion in resistance, particularly regarding storage pests as it affects the rate at which a population can build up.

Feeding trials have also been carried out on *Spodoptera littoralis, Chilo partellus* and *Heliothis armigera* (*Helicoverpa armigera*) in which affinity purified cowpea trypsin inhibitors were added to an artificial larval diet and the subsequent effects on larval development observed.

With all three types of pest, the inhibitor was effective in reducing survival rates and developmental rate both of which are important criteria in crop protection.

CPTI does not appear to be a specific antimetabolite but is effective across a wide range of insect types, that is both Coleoptera and Lepidoptera.

Examples of pests to which the present invention is applicable have been mentioned above. Other important pests to which the invention is applicable include the following:

| Species | |
|---|---|
| Latin Name | Common Name |
| *Sminthurus viridis* | Lucerne Flea |
| *Blatta germanica* | German Cockroach |
| *Locusts migratoria* Spp. | Migratory Locusts |
| *Thrips tabaci* | Onion Thrips |
| *Hodotermes mossambicus* | Harvester Termite |
| *Eurygaster integriceps* Spp. | Wheat Shield Bug |
| *Oebalus pugnax* | Rice Stink Bug |
| *Antestiopsis* Spp. | Coffee Bugs |
| *Helopeltis* Spp. | Helopeltis Bugs |
| *Blissus leucopterus* | Chinch Bug |
| *Distantiella theobroma* | } Cocoa Capsid |
| *Sahlbergella singularis* | |
| *Cicadulina* Spp. | Maize Leafhoppers |
| *Empoasca lybica* | Cotton Jassid |
| *Nephotettix* Spp. | Green Rice Leafhopper |
| *Nilaparvata lugens* | Brown Planthopper |
| *Sogatella farcifera* | White Backed Planthopper |
| *Laodelphax striatellus* | Small Brown Planthopper |
| *Sogotodes orizicola* | American Rice Delphacid |
| *Aeneolamia* & *Mahanarva* Spp. | Sugar Cane Froghoppers |
| *Diaphorina citri* | Citrus Psylla |
| *Bemisia tabaci* | Cotton White Fly |
| *Aleurocanthus woglumi* | Citrus Blackfly |
| *Aphis fabae* | Bean Aphid |
| *Aphis gossypii* | Cotton Aphid |
| *Myzus persicae* | Peach - Potato Aphid |
| *Planococcus citri* | Citrus Mealybug |
| *Aonidiella aurantii* | California Red Scale |
| *Acromyrmex* & *Atta* Spp. | Leaf Cutting Ants |
| *Cephus pymaeus* | Wheat Stem Sawfly |
| *Trogoderma granarium* | Khapra Beetle |

| Species | |
|---|---|
| Latin Name | Common Name |
| Oryzaephilus surinamensis | Saw Toothed Grain Beetle |
| Cosmopolites sordidus | Banana Weevil |
| Lissorhoptrus oryzophilus | Rice Water Weevil |
| Hypothenemus hampei | Coffee Berry Borer |
| Agriotes Spp. | Click Beetles/wireworms |
| Atomaria linearus | Pigmy Mangold Beetle |
| Diabrotica Spp. | Corn Rootworm |
| Meligethes aeneus | Cabbage Blossom Beetle |
| Leptinotarsa decemlineata | Colorado Beetle |
| Phyllotreta Spp. | Flea Beetles |
| Oulema melanopus | Cereal Leaf Beetle |
| Melolontha melolontha | Cockchafer |
| Epilachna varivestis | Mexican Bean Beetle |
| Coryna Spp. | Pollen Beetles |
| Epicauta Spp. | Blister Beetles |
| Pectinophora gossypiella | Pink Boll Worm |
| Phthorimaea operculella | Potato Tuber Moth |
| Leucoptera Spp. | Coffee Leaf Miners |
| Elasmopalpus lignosellus | Lesser Corn Stalk Borer |
| Tryporyza incertulas | Yellow Rice borer |
| Diatraea saccharalis | American Sugar Cane Borer |
| Maruca testulalis | Bean Pod Moth |
| Cnaphalocrocis medinalis | Rice Leaf Roller |
| Buccalatrix thurbiella | Cotton Leaf Perforator |
| Agrotis ipsilon | Greasy Cutworm |
| Alabama argillacea | Cotton Leafworm |
| Diparopsis watersi | Sudan Bollworm |
| Earias citrina | Spiny Bollworm |
| Heliothis virescens | Tobacco Bollworm |
| Sesamia cretica | Pink Borer of Sugar Cane |
| Spodoptera frugiperda | Fall Armyworm |
| Spodoptera littoralis | Cotton Leafworm |
| Trichoplusia ni | Cabbage Looper |
| Plutella xylostella | Diamond Back Moth |
| Laspeyrisa nigricana | Pea Moth |
| Enarmonia pomonella | Codling Moth |
| Choristoneura fumiferna | Spruce Budworm |
| Porthetria dispar | Gypsy Moth |
| Contarinia sorghicola | Sorghum Midge |
| Phytophaga destructor | Hessian Fly |
| Ceratitis capitata | Mediterranean Fruit Fly |
| Atherigona soccata | Sorghum Shoot Fly |
| Leptohylemia coarctata | Wheat Bulb Fly |
| Erioischia brassicae | Cabbage Root Fly |
| Oscinella frit | Frit Fly |
| Panonychus ulmi | European Red Mite |
| Panonychus citri | Citrus Red Mite |
| Tetranychus urticae | Two Spotted Mite |
| Eriophyes sheldoni | Citrus Bud Mite |
| Phyllocoptruta oleivora | Citrus Rust Mite |
| Polyphagotarsanemus latus | White/Broad Mite |
| Acarus Siro | Grain Mite |

As indicated above the invention is applicable to the protection of cotton and cereal crops. Details of crops to which the present invention is applicable are listed more fully below.

Industrial Crops
  Cotton, tobacco, coffee, Soya, groundnuts, oilseed rape

Carbohydrate Sources
  Sugar beet, sugar cane, cassava

Cereals
  Rice, maize, sorghum, wheat, barley

Vegetables
  Potatoes, tomatoes, brassicae

Fruit
  Apples, citrus fruits, grapes

Forestry
  Coniferous and broad-leaved trees

Forage Crops
  Alfalfa.

The term "pesticidally effective" as used herein includes reference not only to killing or injuring pests but also to repelling them.

We claim:

1. A method of protecting a plant or a part of the said plant against an invading pest, comprising presenting a pest belonging to the genus Heliothis, Anthonomus, Tribolium, Sitophilus, Chilo, Spodoptera, Ostrinia or Agrotis with a pesticidally effective amount of a cowpea trypsin inhibitor while the said pest is in contact with or in the vicinity of the said plant or said plant part, wherein the said plant is not a cowpea and does not produce cowpea trypsin inhibitor.

2. The method of claim 1, wherein the said plant is a non-leguminous plant.

3. The method of claim 1, wherein the said pest is *Heliothis Virescens, Heliothis armigera* (*Helicoverpa armigera*) or *Heliothis Zea*.

4. The method of claim 1, wherein the presentation of a pesticidally effective amount of the said cowpea trypsin inhibitor is achieved by external application of the said inhibitor to the said plant or to a part of the said plant or by application of the said inhibitor in the vicinity of the said plant to be protected.

* * * * *